US00PP25717P3

(12) United States Plant Patent
Madsen

(10) Patent No.: US PP25,717 P3
(45) Date of Patent: Jul. 14, 2015

(54) ***RHIPSALIDOPSIS* PLANT NAMED 'PKMRHIPS03'**

(50) Latin Name: *Rhipsalidopsis×hybrida*
Varietal Denomination: PKMRhips03

(71) Applicant: Gartneriet PKM A/S, Odense N (DK)

(72) Inventor: Christian Hald Madsen, Korsør (DK)

(73) Assignee: Gartneriet PKM A/S, Odense N (DK)

( * ) Notice: Subject to any disclaimer, the term of this patent is extended or adjusted under 35 U.S.C. 154(b) by 157 days.

(21) Appl. No.: 13/986,559

(22) Filed: May 15, 2013

(65) Prior Publication Data

US 2014/0345018 P1 Nov. 20, 2014

(51) Int. Cl.
*A01H 5/02* (2006.01)

(52) U.S. Cl.
USPC ..... Plt./372

(58) Field of Classification Search
USPC ..... Plt./372
See application file for complete search history.

(56) References Cited

PUBLICATIONS

Printout of application information from Community Plant Variety Office (CPVO) website for corresponding CPVO application No. 2013/0753 filed Mar. 4, 2013 (1 page) (http://www.cpvoextranet.cpvo.europa.eu).
Printout of application information from Agricultural Production Bureau, Ministry of Agriculture, Forestry and Fisheries website for corresponding Japanese Plant Breeders' Rights application No. 28221 filed May 28, 2013 (1 page). (http://www.hinsyu.maff.go.jp/vips2/cmm/apCMM110.aspx?MOSS=1).

*Primary Examiner* — Susan McCormick Ewoldt
(74) *Attorney, Agent, or Firm* — Foley & Lardner LLP

(57) ABSTRACT

A new and distinct *Rhipsalidopsis* plant named 'PKMRHIPS03' particularly characterized by its compact plant habit; dense and bushy plant form; moderate growth rate and a upright growth habit; purple colored buds; and large, upright purple flower.

3 Drawing Sheets

Latin name of the genus and species of the plant claimed: *Rhipsalidopsis×hybrida.*

Variety denomination: 'PKMRhips03'.

BACKGROUND OF THE INVENTION

The present invention relates to a new and distinct cultivar of *Rhipsalidopsis*, botanically known as *Rhipsalidopsis×hybrida* sometimes referred to as *Rhipsalidopsis* Britton et Rose, including *Epiphylopsis* Berger, commonly known as either Easter Cactus or Spring Cactus, and hereinafter referred to by the cultivar name 'PKMRhips03'.

The new *Rhipsalidopsis* cultivar is a product of a controlled breeding program conducted by the inventor, Christian Hald Madsen, in Søhus, Denmark.

The new *Rhipsalidopsis* cultivar originated from a cross made by the inventor in 2006 in Søhus, Denmark. The female and male parents are unpatented, proprietary *Rhipsalidopsis×hybrida* cultivars. The new *Rhipsalidopsis* cultivar was discovered and selected by the inventor as a single flowering plant within the progeny of the stated cross in a controlled environment in 2010 in Søhus, Denmark. The inventor selected 'PKMRhips03' on the basis of its flower color and compact, freely branching, upright growth habit.

Asexual reproduction of the new *Rhipsalidopsis* cultivar by phylloclade cuttings was first performed in 2010 in Søhus, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'PKMRhips03' which distinguish this *Rhipsalidopsis* as a new and distinct cultivar:

1. Upright growth habit;
2. Red-Purple Flowers (RHS N74D);
3. Moderately vigorous growth; and
4. Red-Purple buds (RHS N74A).

Data on the parent cultivars is no longer available for comparison with the claimed cultivar.

The most similar commercial cultivar to the instant cultivar 'PKMRhips03' is the *Rhipsalidopsis* cultivar 'Andromeda' (unpatented). Plants of the instant cultivar 'PKMRhips03' differ primarily from plants of *Rhipsalidopsis* 'Andromeda' in the following characteristic:

1. Plants of 'PKMRhips03' have a more upright growth habit than plants of 'Andromeda';
2. Plants of 'PKMRhips03' have yellow-green phylloclades (closest to RHS 147A) whereas plants of *Rhipsalidopsis* 'Andromeda' have darker green phylloclades (between to RHS 137A and RHS 137B);
3. Plants of 'PKMRhips03' have tepals colored red-purple, RHS N74D whereas plants of *Rhipsalidopsis* 'Andromeda' have tepals colored red-purple, between RHSN74 B and RHS N74C; and
4. Plants of 'PKMRhips03' have a green colored ovary (RHS 138A) whereas plants of *Rhipsalidopsis* 'Andromeda' have a yellow-green colored ovary (between RHS 146A and RHS 146B)

BRIEF DESCRIPTION OF THE PHOTOGRAPHS

The accompanying photographs illustrate the overall appearance of the new *Rhipsalidopsis* cultivar 'PKMRhips03' showing the colors as true as is reasonably possible with colored reproductions of this type. Colors in the photographs may differ slightly from the color values cited in the detailed botanical description, which accurately describe the color of 'PKMRhips03'.

Figure 1:
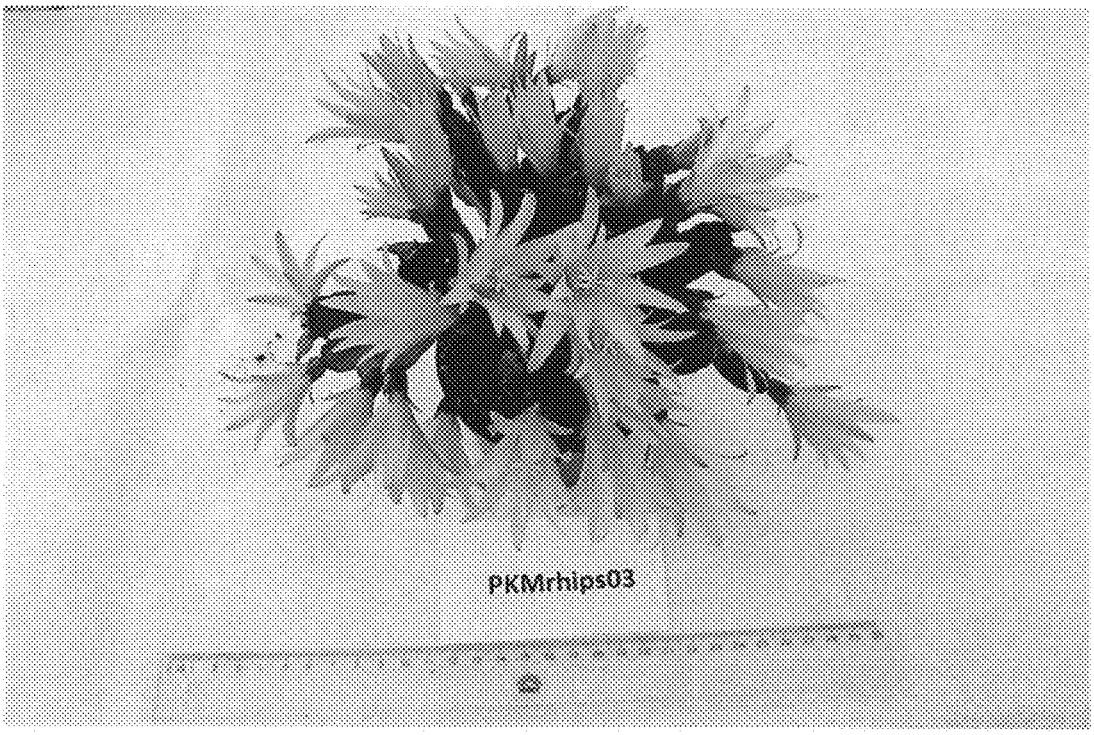
FIG. 1 shows a typical flowering plant of 'PKMRhips03' grown in a 5 cm pot.
Figure 2:
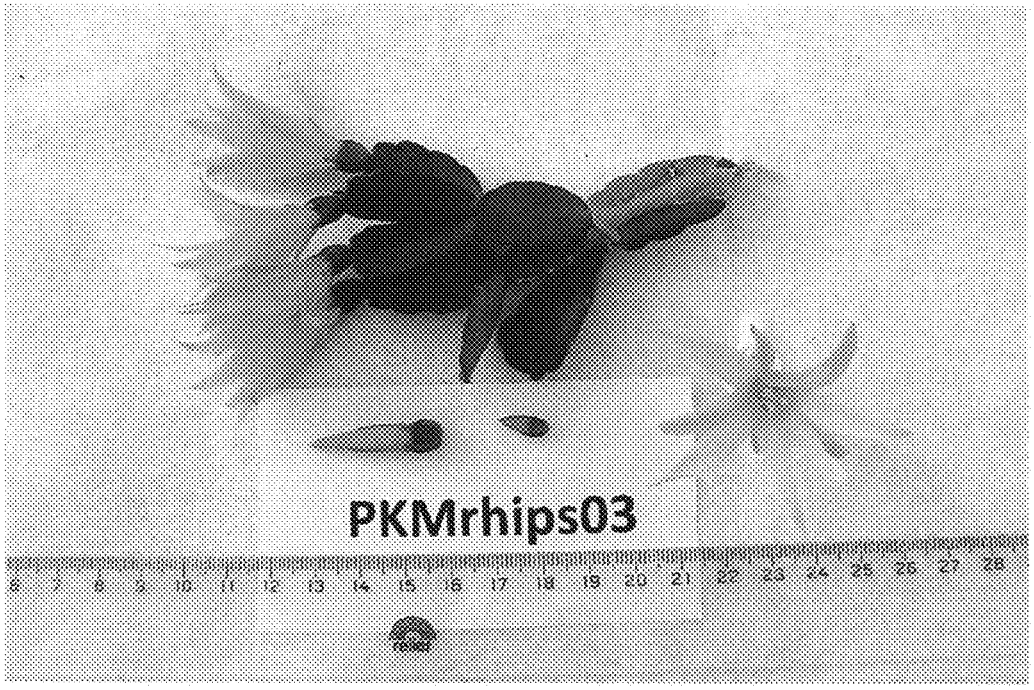
FIG. 2 shows a close-up view of typical buds and flowers and a single phylloclade of 'PKMRhips03'.
Figure 3:
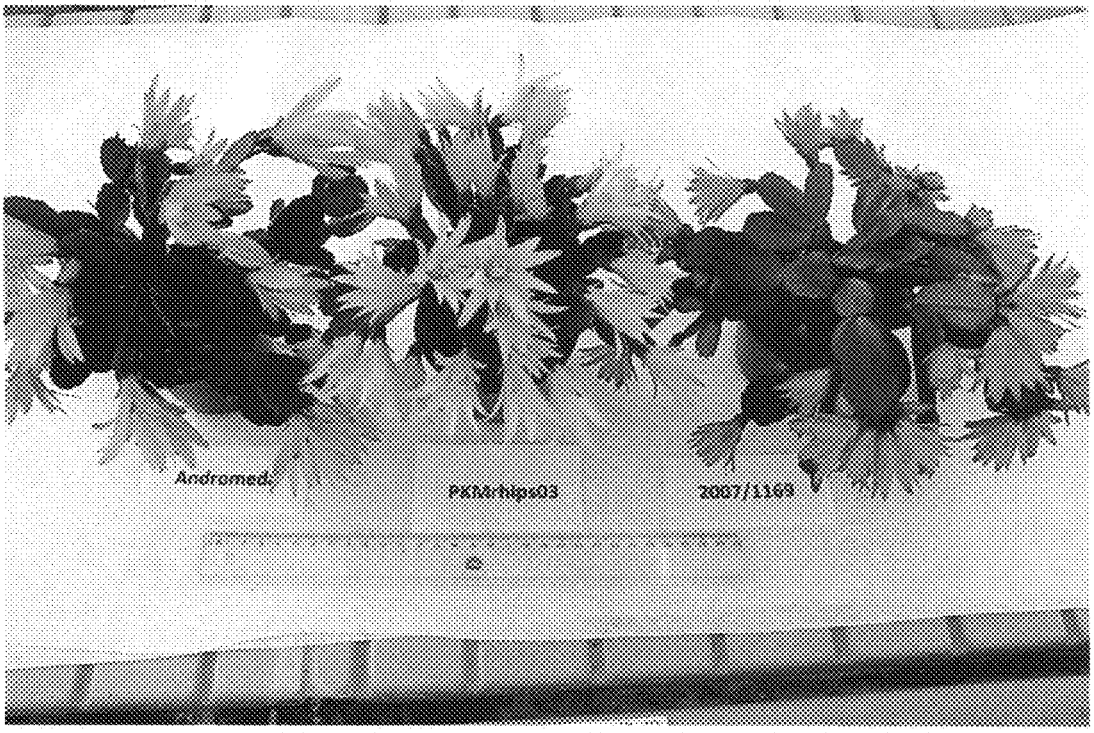

FIG. 3 shows a comparison of a typical plant of 'PKMRhips03' with a typical plant of the comparison variety 'Andromeda' and with another comparison *Rhipsalidopsis* variety '7304G' (labelled with its CPVO application No. '2007/1169'; U.S. Plant Pat. No. 21,238.)

DETAILED BOTANICAL DESCRIPTION

The new *Rhipsalidopsis* cultivar 'PKMRhips03' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'PKMRhips03' as grown in a glass-covered greenhouse in Fyn, Denmark, under conditions which closely approximate those generally used in commercial practice, where day temperatures in the greenhouse average 18° C. and night temperatures in the greenhouse average 16° C. Ambient light levels used while growing plants of 'PKMRhips03' are +50 $Wm^2$. No growth retardants were used when growing plants of 'PKMRhips03'.

The age of the 'PKMRhips03' plants described is 10-12 months old and grown in 5 cm pots. The photographs and descriptions were taken during the winter season. Color references are made to The Royal Horticultural Society Colour Chart (R.H.S.), $5^{th}$ edition, except where general colors of ordinary significance are used.

Classification:

*Botanical.*—*Rhipsalidopsis* Britton et Rose.

*Common name.*—Easter Cactus or Spring Cactus.

*Variety denomination.*—PKMRhips03.

Parentage:

*Female or seed parent.*—Unpatented, proprietary *Rhipsalidopsis* Britton et Rose cultivar.

*Male or pollen parent.*—Unpatented, proprietary *Rhipsalidopsis* Britton et Rose cultivar.

Propagation: By phylloclade cuttings.

*Time and temperature to initiate roots.*—In a greenhouse, about 2 months at 18° C. to 21° C.

*Rooting habit and description.*—Fine, well-branched.

Plant:

*Type.*—Perennial, Epiphyte.

*Overall shape.*—Upright.

*Form.*—Dense and Bushy.

*Growth habit.*—Branched.

*Branching habit.*—Three new phylloclades forming at the apical end of older phylloclades. No pinching required.

*Growth rate.*—Slow.

*Vigor.*—Moderate.

*Crop time.*—About 10-12 months are required to produce a finished flowering plant.

*Size at maturity.*—Height (soil level to top of plant, including flowers): About 7-8 cm. Spread: About 8 to 10 cm.

Stem: None, older phylloclades may turn woody with age (several years).

Phylloclade:

*Arrangement.*—Phylloclades form at the apex of older phylloclades to form branches.

*Aspect.*—Upright to arching (from basal phylloclade).

*Strength.*—Strong (from basal phylloclade).

*Length.*—About 20-40 mm.

*Width.*—Up to 22 mm.

*Overall shape.*—Oval.

*Apex shape.*—Truncate.

*Base shape.*—Rounded.

*Margin.*—Crenate. Can be purple, between RHS 83A and RHS 83B.

*Texture.*—Glabrous, smooth.

*Pubescence.*—Approx. 1-5 hairs up to 4 mm long at areoles along margins.

*Color of mature phylloclade.*—Upper and lower surfaces: RHS 147A, yellow-green, the central part can be a little brighter.

*Venation.*—None.

Flower description:

*Natural flowering season.*—Flowering occurs from February to April (northern hemisphere), but can be changed by short day photo-treatment and cold treatment. Flowers persistent, sessile.

*Flowering response time.*—About 8 to 9 weeks after end of cold treatment.

*Flowering longevity* (*dependent on temperature and light conditions*).—About 5 to 6 days.

*Fragrance.*—None.

*Quantity of flowers per terminal phylloclade.*—About 1 to 3.

*Quantity of flowers and buds per plant.*—About 20 to 30, depending on plant size.

*Flower bud.*—Length: Ranging from 0 to 25 mm (before anthesis). Width: Ranging from 0 to 1 cm. Shape: Ovoid to lanceolatoid. Color: Larger Buds (over 1 cm): RHS N74A, Red-Purple. Smaller Buds (up to 1 cm): Between RHS N74A and N74B, Red-Purple.

*Flower.*—Type: Single. Shape: Actinomorphic. Aspect: Upright to vertical during development. Persistent or self-cleaning: Persistent. Height: About 3.0 cm to 3.5 cm (including ovary). Diameter: Up to 7.5 cm.

*Tepals.*—Arrangement: Actinomorphic; not fused. Quantity: 15-20. Length: Ranging from 3 mm to 35 mm. Width: Ranging from 0 mm to 5 mm. Shape: Oblanceolate. Apex: Acute. Base: Apical Whorl: Fused. Basal Whorl: Free. Margin: Entire. Appearance: Matte. Texture: Smooth and Silky. Color (When Opening): Upper and lower surfaces: RHS N74A, red-purple. Color (When Fully Opened): Upper and lower surfaces: RHS N74D, red-purple. Color Fades to: RHS 61A, red-purple.

Reproductive organs:

*Androecium*.—Stamen: Quantity: Many (>100). Anther: Shape: Oblong. Length: About 1 mm. Color: RHS 17A, yellow-orange. Filament: Length: 15 mm. Color: RHS N74A, red-purple. Pollen: Amount: Plenty. Color: RHS 17A, yellow-orange.

*Gynoecium*.—Pistil: Quantity: 1. Stigma: Shape: Ovoid. Color: Between RHS 155A and RHS 155B, white. Style: Length: 15 mm. Color: Base: RHS NN155C, white. Apex: RHS N74A, red-purple. Ovary: Shape: obdeltoid with a broad base. With ribs. Length: 6 mm. Width: 8 mm. Color: RHS N138A, green.

Seeds/fruit: None observed.

Disease/pest resistance and susceptibility: Not tested.

Temperature tolerance: Tolerant to a low temperature of about 2° C. and to a high temperature about 40° C.

I claim:

1. A new and distinct *Rhipsalidopsis* plant named 'PKMRHIPS03', as illustrated and described herein.

* * * * *